United States Patent [19]

Adekunle et al.

[11] Patent Number: 5,296,225
[45] Date of Patent: Mar. 22, 1994

[54] INDIRECT METHOD OF TREATING OROFACIAL PAIN

[76] Inventors: Michael Adekunle, 1660 N. Prospect Ave., #705, Milwaukee, Wis. 53202; James L. Flowers, 10917 N. San Marino Dr., Mequon, Wis. 53092

[21] Appl. No.: 967,364

[22] Filed: Oct. 28, 1992

Related U.S. Application Data

[63] Continuation-in-part of Ser. No. 870,510, Apr. 17, 1992, Pat. No. 5,178,879.

[51] Int. Cl.5 ............................ A61K 35/78; A61K 9/00
[52] U.S. Cl. ................................. 424/195.1; 424/484; 514/944
[58] Field of Search ........................ 424/484, 195.1; 514/817

[56] References Cited

U.S. PATENT DOCUMENTS

| | | | |
|---|---|---|---|
| 4,313,958 | 2/1982 | LaHann | 424/324 |
| 4,486,450 | 12/1984 | Bernstein | 424/324 |
| 4,536,404 | 8/1985 | Bernstein | 514/627 |
| 4,546,112 | 10/1985 | LaHann et al. | 514/627 |
| 4,557,934 | 12/1985 | Cooper | 514/635 |
| 4,997,853 | 3/1991 | Bernstein | 514/627 |
| 5,008,289 | 4/1991 | Bernstein | 514/627 |
| 5,045,565 | 9/1991 | Gardner | 514/620 |
| 5,134,166 | 7/1992 | Bernstein | 514/627 |

*Primary Examiner*—Thurman K. Page
*Assistant Examiner*—Sally Gardner
*Attorney, Agent, or Firm*—Quarles & Brady

[57] ABSTRACT

The invention relates to a method of treating orofacial pain in a patient wherein an effective amount of capsaicin is topically applied to the skin of the face and/or the neck and/or the scalp overlying the trigeminal or upper cervical nerves and it is left in place for a time sufficient to relieve the symptoms thereof.

2 Claims, No Drawings

_5,296,225_

INDIRECT METHOD OF TREATING OROFACIAL PAIN

RELATED CASE

This application is a continuation-in-part of our co-pending patent application U.S. application Ser. No. 07/870,510 filed Apr. 17, 1992, now U.S. Pat. No. 5,178,879.

FIELD OF THE INVENTION

The present invention relates to a novel indirect method of treating orofacial pain.

BACKGROUND OF THE INVENTION

Orofacial pain represents a huge morbidity for millions of Americans. Tooth pain alone represents significant morbidity with millions having toothaches on a daily basis. In addition, the TMJ syndrome and orofacial myofacial pain may affect up to 10–15% of the population.

Numerous etiologies of facial pains have been described. These include typical pains of dental origin, myopathic pains, neurogenic pains, vascular associated pains, atypical facial pains and sinus related pains. These pains are typically considered to be deep pains requiring interventions which are systemic or direct topical treatments or invasively or surgically directed treatments at the site of pain. The treatments have included ear drops (placed into the ear for ear pain), topical solutions (applied directly to the gums and teeth for tooth pain), local injections (into gums for tooth pain or into trigger points), a variety of systemic analgesics (aspirin, acetaminophen, non-steroidal anti-inflammatory agents and narcotics), a variety of other systemic agents (steroids, diphenylhydantoin, carbamazepine, calcium channel blockers, beta-blockers, and tricyclic antidepressants) and surgical procedures (tooth extractions, sinus operations, etc.).

Although some reasonable treatments are available, no simple, cutaneously applied, rapidly acting and effective treatment has been described to date for the deeper orofacial pains.

BRIEF SUMMARY OF THE INVENTION

It is the primary object of the present invention to disclose a novel indirect method for treating orofacial pain.

We have made the unexpected discovery that orofacial pain in a patient can be treated by an indirect method which comprises topically applying a preparation containing an effective amount of capsaicin to the surface of the skin above the trigeminal and upper cervical nerves, i.e., the caudal and dorsal face and/or head and/or neck and/or anterior scalp areas of the patient. The preparation is left in place for a time sufficient to relieve the symptoms and it may be applied daily or more often.

Capsaicin (trans-8-methyl-N-vanillyl-6-nonenamide) is the pungent principal of red peppers. It is believed to act on a subset of primary afferent nerves mostly of the c-fiber type. It binds to a receptor at the nerve ending and causes a release of substance P. There are believed to be two phases of action, first excitation and then desensitization of the nerve to nociceptive impulses. The excitation results in the "hot" of hot peppers or a burning/tingling sensation when applied to the skin. The desensitization results from depletion of substance P and interference with afferent transmission in a non-tetrodotoxin dependent manner. Clinically, the overall effect is pain relief.

Additionally, several other effects are important. Substance P also exerts an efferent function by causing vasodilation of blood vessels, enhancement of cycloxygenase (and the production of prostaglandins), degranulation of mast cells (the release of histamine), and enhances conversion of kininogens to bradykinin. These effects result in increased nociceptive transmission and significant inflammation. The depletion of substance P blocks these effects. Also, afferent nerves have multiple branches and collaterals, all of which are not fully appreciated. Also, visceral and nerves to deeper structures (such as the deep facial structures) have branches which arise from these deep and cutaneous structures and end up at similar ganglia and central terminations. The full effect of this is not entirely known, but has been used to partially explain the phenomenon of referred pain. Also, afferent nerves have multiple branches and collaterals all of which are not fully appreciated. It is believed that when capsaicin is applied to the skin ending of a peripheral nerve, it can deplete substance P throughout the nerve's course, including its central terminal in the dorsal horn of the spinal cord.

Furthermore, it has been demonstrated that interruption of the nerve to the referred site of pain can block the pain from the deeper structure. The trigeminal nerve (cranial nerve V) is the sensory nerve for the cutaneous and deep structures for most of the face and the anterior scalp. The cervical nerves subserve some of the caudal and dorsal face and head and neck structures.

The description and examples which follow will make it apparent to those skilled in the art, that the above object and other objects and advantages are obtained by the practice of the present invention.

DESCRIPTION OF THE PREFERRED EMBODIMENTS

In the preferred practice of the invention, a gel containing 0.05% capsaicin is applied one or more times to the caudal and dorsal face and/or head and/or neck and/or anterior scalp structures of a patient suffering from orofacial pain. The gel is applied and left in place until the symptoms are relieved. The applications may be daily or more often if required.

The invention is further illustrated by the following examples.

EXAMPLES

EXAMPLE 1

A female in her 30's was visiting from Alaska. A prior root canal filling suddenly was dislodged. There was sudden increased pain. Aspirin was tried without relief. The tooth was in the right lower posterior quadrant. A 0.05% capsaicin gel (CAPSAGEL TM -IYATA Pharmaceuticals, Inc., Milwaukee, Wis.) was applied on the skin of the face over the location of the tooth and the pain. Relief ensued rapidly and was nearly complete. Four hours later, she was able to see a dentist who was able to do some invasive work and replace the filling. No additional anesthesia was required.

EXAMPLE 2

A 37-year-old female had a filling fall out of her left upper front molar. She consulted aa dentist who anesthetized the area by injection. Invasive work was done and was described by the patient as being cleaning, "digging," and "sawing." A temporary cap was placed. The patient was instructed to return two weeks later for follow-up. Two hours after leaving the dentist, pains increased with burning and throbbing in the area of the tooth. She was unable to open her mouth fully and was unable to talk. No oral medications were used. 0.05% capsaicin gel (CAPSAGEL TM) was applied on the facial skin over an area from the upper cheek to the corner of the lip where the pain was felt. Within five minutes, the patient could open and close her mouth. Within 10 minutes, she was able to talk and the pain was gone. She was able to drink cold water without difficulty. Excellent relief persisted for 7-8 hours. About midnight, the tingling sensation began to reappear, she immediately applied the gel again and relief ensued within five minutes and persisted all night. No adverse effects were reported.

EXAMPLE 3

A 34-year-old female had severe earaches for three years. Both ears were affected. The episodes would occur from one to three times per month and would last from hours to days. The pain was felt inside the ear and was sharp. Her hearing was normal and there was no associated vertigo. She had been evaluated by her family physician, by two different ear-nose-throat specialists and by dentists. They all told her they could find no etiology for the pain. She had tried aspirin, heating pads, eardrops and acetaminophen with codeine (No. 3), all without help. A 0.025% capsaicin gel (CAPSAGEL TM) was applied to the area of the skin and scalp anterior and inferior to the earlobe. Within 15-20 minutes relief of pain began that rapidly progressed to complete relief which lasted for the whole day. She reported no adverse effects from the application.

EXAMPLE 4

A 42 year old female had a filling fall out and had pain in the upper left dental quadrant for three weeks. Over-the-counter analgesics were not effective. She was unable to eat sweets without discomfort. A capsaicin gel 0.5% (Capsagel) was applied over the area of the upper left cheek overlying the toothache. Within 15 minutes the pain had resolved. She was able to eat sweets without difficulty.

EXAMPLE 5

A 19 year old female contracted a viral syndrome. Symptoms included fever, nasal congestion, generalized malaise and sore throat resulting in dysphagia. A capsaicin gel 0.05% (Capsagel) was applied to the neck anteriorly from the submandibular area to the sternal notch. Throat discomfort subsided within 20 minutes. Swallowing was possible with minimal discomfort. Relief persisted for 5-6 hours. A reapplication provided similar relief.

EXAMPLE 6

A 42 year old female had the onset of a viral syndrome. Symptoms included severe sore throat, nasal congestion, generalized malaise, and cough. Acetaminophen provided partial relief. A capsaicin gel 0.05% (Capsagel) was applied to the anterior neck from the sternal notch to the submandibular area. Relief ensued within 15 minutes and persisted for over 5 hours.

In addition to the foregoing patients, other individuals have used the capsaicin containing topical preparations cutaneously and topically for tension headaches, TMJ pains and sinus pains and achieved partial to nearly complete relief.

Any topical preparation containing a concentration of synthetic or natural capsaicin of about 0.01% to about 0.1% can be used. However, gel preparations containing about 0.025% to about 0.075% of capsaicin are preferred. The preparation also may be a suspension, spray, lotion, liquid, roll-on, gel stick, etc., and it may contain benzocaine or similar topical anesthetic to decrease burning sensation. It also can contain coloring agents and fragrances.

The capsaicin containing topical preparation especially preferred for use in the present invention is the 0.05% capsaicin gel, CAPSAGEL TM which is distributed by IYATA Pharmaceuticals, Inc. of Milwaukee, Wis. In addition to the gel, an ointment or cream containing 0.025% of capsaicin is available under the trademark ZOSTRIX.

The advantages of the method of the present invention are that it provides relief of orofacial pain by the simple topical application of a capsaicin containing preparation to the skin of the face and/or neck and/or the scalp of the patient. The onset of effectiveness is rapid and can be measured in minutes. It also has a relatively prolonged duration of action which is measured in hours to days and it has only minimal side effects due to the topical administration.

The term "orofacial" as used in the present application is intended to cover tension headaches, TMJ pains, sinus pain, toothaches, orofacial mylofacial pain, and non-arthritic, non-musculoskeletal, cervical neck pain originating deep in cervical structure and having similar etiologies and treatment.

It will be apparent to those skilled in the art that a number of modifications and changes can be made without departing from the spirit and scope of the present invention. Therefore, it is intended that the invention be limited only by the claims.

We claim:

1. A method of treating an orofacial pain selected from ear pain and TMJ pain in a patient having such a pain which consists essentially of topically applying a preparation consisting essentially of about 0.025 to about 0.075% of capsaicin in a pharmaceutically acceptable carrier selected from the group consisting of a lotion, a cream, a gel, and an ointment to the skin of the patient overlying the trigeminal and cervical nerves which lead to the area of pain.

2. The method of claim 1 wherein the preparation further comprises benzocaine.

* * * * *